United States Patent [19]

Shutske

[11] Patent Number: 4,668,690
[45] Date of Patent: May 26, 1987

[54] 1,2,3,4,4A,9B-HEXAHYDRO-4A-AMINOALK-YLDIBENZOFURANS USEFUL AS ANALGESICS, ANTICONVULSANTS OR ANTIDEPRESSANTS

[75] Inventor: Gregory M. Shutske, Somerset, N.J.

[73] Assignee: Hoechst Roussel Pharmaceuticals Inc., Somerville, N.J.

[21] Appl. No.: 814,453

[22] Filed: Dec. 30, 1985

[51] Int. Cl.$^4$ .................. A61K 31/34; C07D 307/91
[52] U.S. Cl. .............................. 514/320; 514/222;
514/227; 514/253; 514/378; 514/256; 514/337;
514/381; 514/365; 514/372; 514/383; 514/374;
514/397; 514/406; 514/422; 514/444; 514/468;
544/60; 544/63; 544/96; 544/153; 544/238;
544/333; 544/375; 544/405; 546/196; 546/269;
548/203; 548/214; 548/235; 548/247; 548/255;
548/262; 548/336; 548/374; 548/525; 549/60;
549/460; 564/442
[58] Field of Search ............ 549/60, 460; 514/468,
514/222, 227, 253, 256, 320, 337, 365, 372, 374,
378, 381, 383, 397, 406, 422, 444; 544/60, 63,
96, 153, 238, 333, 375, 405; 546/196, 269;
548/203, 214, 235, 247, 255, 262, 336, 374, 525

[56] References Cited

U.S. PATENT DOCUMENTS 3,496,181 2/1970 Skaletsky et al. ............... 549/460
4,409,221 10/1983 Lombourieu et al. ............ 549/460

OTHER PUBLICATIONS

Cassis et al., J. Heterocyclic Chem., 21, p. 869, (1984).
Burke, Jr. et al., J. Org. Chem., 49, p. 2508, (1984).
Mokatoff et al., J. Org. Chem. 33(9), p. 3551, (1968).
Schultz et al., J. A. C. S. 99, p. 8065, (1977).
Martin et al., J. Org. Chem. 46, p. 3567, (1981).
Martin et al., J. Org. Chem., 47, p. 1513, (1982).

Primary Examiner—Henry R. Jiles
Assistant Examiner—Bernard I. Dentz
Attorney, Agent, or Firm—Jerome Rosenstock

[57] ABSTRACT

This invention relates to 1,2,3,4,4a,9b-hexahydro-4a-aminoalkyldibenzofurans of the formula

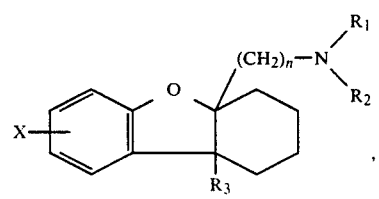

where X is hydrogen, loweralkyl, F and Cl; $R_1$ is hydrogen, loweralkyl, arylloweralkyl, loweralkenyl, loweralkoxyloweralkyl, aryloxyloweralkyl, cycloalkylloweralkyl and heteroarylloweralkyl; $R_2$ is hydrogen, lower alkyl or $R_1$ and $R_2$ taken together with the N ring atom constitute a saturated or unsaturated heterocyclic ring having 5 or 6 members; $R_3$ is hydrogen, lower alkyl; n is an interger of 1 to 3; and the pharmaceutically acceptable acid addition salts thereof and where applicable the stereo, optical and geometrical isomers of the foregoing.

38 Claims, No Drawings

1,2,3,4,4A,9B-HEXAHYDRO-4A-AMINOALKYL-DIBENZOFURANS USEFUL AS ANALGESICS, ANTICONVULSANTS OR ANTIDEPRESSANTS

This invention relates to novel compounds of the formula

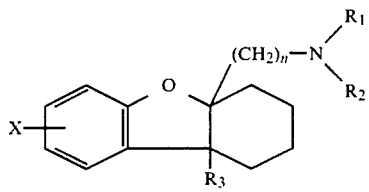

where X is hydrogen, loweralkyl, F, and Cl; $R_1$ is hydrogen, loweralkyl, arylloweralkyl, loweralkenyl, loweralkoxyloweralkyl, aryloxyloweralkyl; cycloalkylloweralkyl and heteroarylloweralkyl; $R_2$ is hydrogen, loweralkyl or $R_1$ and $R_2$ taken together with the N constituent constitute a saturated heterocyclic ring having 5 or 6 members; $R_3$ is hydrogen, loweralkyl; n is an integer of 1 to 3; and the pharmaceutically acceptable acid addition salts thereof and where applicable the stereo, optical and geometrical isomers of the foregoing.

To the best of our knowledge the compounds of the present invention have not been described or suggested.

Throughout the specification and the appended claims, a given chemical formula or name shall encompass all stereo optical, and geometrical isomers thereof where such isomers exist, as well as pharmaceutically acceptable acid addition salts thereof and solvates thereof, such as for instance hydrates.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc; the term "arylloweralkyl" refers to a monovalent substituent which consists of an aryl group, e.g., phenyl, o-toluyl, m-methoxyphenyl, etc. linked through a lower alkylene group having its free valence bond from a carbon of the lower alkylene group, and having a formula of

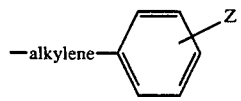

where Z is hydrogen, halogen, loweralkyl, loweralkoxy, $CF_3$, and $NH_2$; the term "alkylene" refers to a bivalent radical of the lower branched or unbranched alkyl group it is derived from having valence bonds from two terminal carbons thereof, e.g. ethylene ($-CH_2-CH_2-$), propylene ($-CH_2CH_2CH_2-$), isopropylene

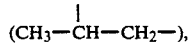

etc; the term "alkenyl" refers to a straight or branched chain hydrocarbon containing one unsaturated or double bond, e.g. $CH_2=CH-$, $CH_3CH=CH-$,

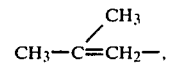

etc.; the term "alkoxy" or "aryloxy" refers to a substituent which consists of an alkyl group or an aryl group, respectively, linked through an ether oxygen having its free valence bond from the ether oxygen, e.g. methoxy, ethoxy, propoxy, butoxy, pentoxy, etc. and accordingly, the term "loweralkoxyloweralkyl" would encompass an alkoxy group linked through an alkylene linkage, e.g. $CH_3OCH_2-$; and the term "aryloxyloweralkyl" would encompass an aryloxy group linked through an alkylene linkage, e.g.

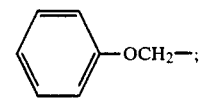

the term "cycloalkylloweralkyl" refers to a monovalent substituent consisting of a saturated hydrocarbon group possessing at least one carbocyclic ring of 3 to 7 carbon atoms, e.g. cyclopropyl, cyclobutyl, cyclopentyl, cyclohexyl, cycloheptyl, etc., linked through a lower alkylene group; and the term "heteroarylloweralkyl" refers to a monovalent substituent consisting of an unsaturated ring compound containing at least one atom other than carbon, such as N, O, S, P, Se, As, e.g. furanyl, thienyl, pyrrolyl, pyrazolyl, imidazolyl, triazolyl, pyridinyl, pyridazinyl, pyrimidinyl, pyrazinyl, oxazinyl, oxazolyl, isoxazolyl, thiazolyl, isothiazolyl etc., linked through a lower alkylene group, e.g. methylene, ethylene, propylene, etc.

As defined above, $R_1$ and $R_2$ taken together with the N ring atom constitute a saturated heterocyclic ring having 5 or 6 members. This definition is meant to encompass heterocyclic ring systems containing the already existing N atom and in addition zero, or one or more of the same or different heterocyclic atoms and encompasses such ring substituents as piperidyl, pyrrolidyl, morpholino, thiomorpholino, piperazinyl, etc.

The compounds of the present invention are prepared in the following manner. The substituents, X, $R_1$, $R_2$, $R_3$ and the integer n are as defined above unless indicated otherwise.

A substituted cyclohexanone of the formula II is selected

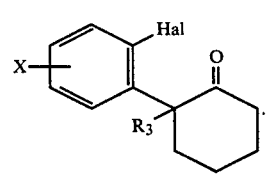

The term "Hal" as used here and hereinafter refers to a member of the halogen family consisting of fluorine, chlorine, bromine and iodine. These cyclohexanone compounds are readily available or can be readily prepared such as by D. Dieterich in "Methoden der Organischen Chemie" (Houber-Weyl); Georg Thieme Verlag: Stuttgart, West Germany, 1973; Band VII/2a, Teil 1, pp 932–942.

Compound II is treated with an organometallic halide of the formula, $R_1-N-(CH_2)_3M$ (III); where M is Li or Mg Hal and treating the resultant product with a suitable protic compound, such as water, in a conventional manner, to form alcohol IV(a) of the formula

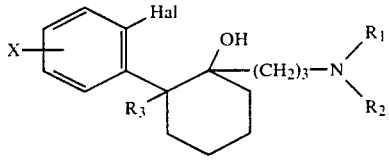

Typically the reaction of Compound II with reagent III is carried out at a temperature of 0° to 85° C. for 1 to 8 hours, in an inert anhydrous solvent, e.g. tetrahydrofuran, diethyl ether, 1,2-dimethoxy ethane, etc. The hydrolysis is typically carried out at a temperature of 0° to 25° C., for 5 to 30 minutes.

Compound II is reacted with a dialkyl acetamide of the formula

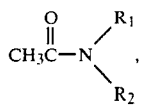

in the presence of lithiumdiisopropylamide at a temperature of −70° to 25° C. for 0.5 to 8 hours in an inert anhydrous solvent, e.g. tetrahydrofuran, diethyl ether, 1,2-dimethoxy ethane, etc. to form alcohol XI of the formula

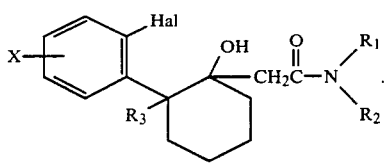

Compound XI in turn is reacted with a suitable reducing agent, such as lithium aluminum hydride, sodium bis-(3-methoxyethoxy)aluminum hydride, etc., under standard reaction conditions, typically at a temperature of 0° to 80° for 1 to 4 hours in a suitable solvent, e.g. tetrahydrofuran, diethyl ether, toluene, etc., to form an alcohol of the formula

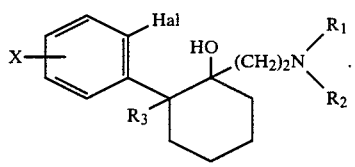

Compound II is reacted with a compound of the formula

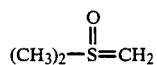

to form an epoxide having the formula

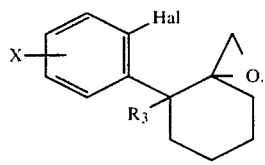

This reaction is typically carried out at a temperature of 0° to 100° C. for 0.5 to 5 hours in a polar aprotic solvent, e.g. tetrahydrofuran (THF), dimethylsulfoxide (DMSO), dimethylformamide (DMF), etc. Compound XII in turn is reacted with an amine of the formula $HN(R_1)(R_2)$ (XIII) to form an alcohol of the formula

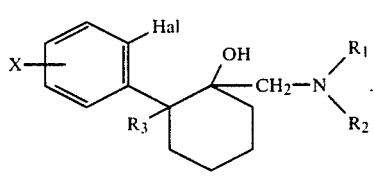

Typically this reaction is carried out at a temperature of 25° to 120° C. for 2 to 12 hours without a solvent.

Compounds IV(a), (b), (c), are typically treated with a strong base, e.g. NaH, phenyllithium, KH, lithium diisopropyl amide, etc., at a temperature of 80° to 150° C. for 1 to 6 hours, in a inert solvent, e.g. benzene, toluene, DMF, etc. to affect ring closure to form Compound I of the invention.

Compound I of the invention, where at least $R_1$ is hydrogen, is obtained by reacting compound I, where $R_1$ and $R_2$ are other than hydrogen, with phenyl chloroformate and then decomposing the resulting carbamate to give the secondary amine, employing standard conditions well known in the art. The compound thus obtained is reacted with an acid halide of the formula

where $R_4$ is aryl, aryloweralkyl, loweralkenyl, aryloxyloweralkyl, cycloalkyl, cycloalkylloweralkyl, heteroaryl and heteroarylloweralkyl to form Compound VI of the formula

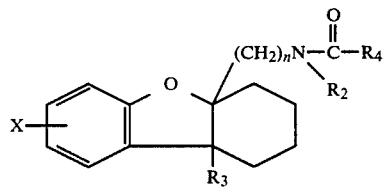

Compound VI is typically obtained by reacting Compound I, where $R_1$ is H, with the Compound V in the presence of an inert solvent, such as chloroform, methylene chloride, benzene, toluene, etc., at a temperatue of 0° to 80° C. for 30 to 120 minutes.

Compound VI is then reduced under conventional conditions with suitable reducing reagents, such as metal hydrides, e.g. lithium aluminum hydride, sodium bis(2-methoxyethoxy)aluminum hydride, etc., under standard reaction conditions, typically at a temperature of 0° to 80° C. for 1 to 4 hours in a suitable solvent, e.g.

tetrahydrofuran, diethyl ether, toluene, etc., to form Compound VII of the invention

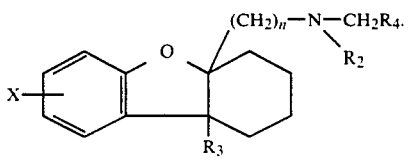

Compound I of the invention, where at least $R_1$ is hydrogen, is reacted with a halide of the formula Hal-$R_5$ (VIII), where $R_5$ is loweralkyl, arylloweralkyl, loweralkenyl, alkoxyalkyl, aryloxyalkyl, cycloalkylloweralkyl, and heteroarylloweralkyl to form a compound of the invention having the formula

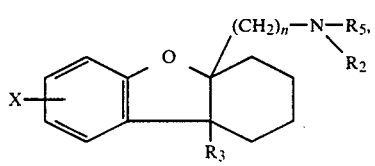

Compound IX is typically obtained by reacting Compound I where $R_1$ is hydrogen with Compound VIII under nucleophilic reaction conditions, e.g. in the presence of an inert solvent, such as methanol, ethanol, acetone, etc., at a temperature of 0° to 150° C. for 1 to 8 hours.

All other starting materials shown above are either known compounds or are easily prepared by routine methods known to the art from readily available materials.

Compounds of the invention include 8-chloro-4a-(3-dimethylaminopropyl)-1,2,3,4,4,4a,9b-hexahydrodibenzofuran; 1,2,3,4,4a,9b-hexahydro-8-methyl-4a-[2-[N-methyl-N-(3-ethoxypropyl)]aminoethyl]dibenzofuran; 1,2,3,4,4a,9b-hexahydro-4a-[3-(N-cyclohexylmethyl-N-methyl)aminopropyl]dibenzofuran; 1,2,3,4,4a,9b-hexahydro-4a-(3-(pyrrol-1-yl)propyl)dibenzofuran; and 1,2,3,4,4a,9b-hexahydro-4a-(3-(thiazol-2-yl)ethyl)dibenzofuran.

The compounds of the invention are primarily useful as analgesic, anticonvulsant and antidepressant agents. The compounds of the invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1953)]. Listed below in Table I is the analgesic effect of some of the compounds of the invention, expressed as percent inhibition of phenyl-para-quinone induced writhing.

TABLE I

| Compound | Dose (subcutaneous) mg/kg | % Inhibition |
|---|---|---|
| cis-4a-(3-dimethylaminopropyl)-1,2,3,4,4a,9b-hexahydro-dibenzofuran hydrochloride | 12.2 | 50 ($ED_{50}$) |
| cis-1,2,3,4,4a,9b-hexahydro-4a-(3-methylaminopropyl)-dibenzofuran hydrochloride | 25 | 58 |
| cis-1,2,3,4,4a,9b-hexahydro-4a-(2-dimethylaminoethyl)-dibenzofuran hydrochloride | 25 | 67 |
| cis-1,2,3,4,4a,9b-hexahydro-4a-(2-methylaminoethyl)-dibenzofuran hydrochloride | 16.2 | 50 ($ED_{50}$) |
| cis-1,2,3,4,4a,9b-hexahydro-4a-[3-(N—methyl-N—phenethylamino)-propyl]dibenzofuran hydrochloride | 20.8 | 50 ($ED_{50}$) |
| cis-1,2,3,4,4a,9b-hexahydro-4a-dimethylaminomethyldibenzofuran hydrochloride | 21.7 | 50 ($ED_{50}$) |
| cis-1,2,3,4,4a,9b-hexahydro-4a-methylaminomethyldibenzofuran hydrochloride | 25.8 | 50 ($ED_{50}$) |
| cis-1,2,3,4,4a,9b-hexahydro-4a-[2-(N—methyl-N—phenethyl)amino ethyl]-dibenzofuran hydrochloride | 25 | 63 |
| cis-1,2,3,4,4a,9b-hexahydro-4a-[2-N—(3-phenylpropyl)-N—methylamino]-ethyl]dibenzofuran oxalate hemihydrate | 7.3 | 50 ($ED_{50}$) |
| cis-1,2,3,4,4a,9b-hexahydro-4a-[2-[N—methyl-N—(3-phenoxypropyl)]aminoethyl]dibenzofuran oxalate hemihydrate | 25 | 65 |
| cis-1,2,3,4,4a,9b-hexahydro-4a-(3-piperidinopropyl)dibenzofuran oxalate | 25 | 64 |
| cis-1,2,3,4,4a,9b-hexahydro-4a-[3-(N—(3-phenylpropyl)-N—methyl)aminopropyl]dibenzofuran oxalate hydrate | 25 | 37 |
| cis-1,2,3,4,4a,9b-hexahydro-4a-[3-(N—methyl-N—furfuryl)amino propyl]dibenzofuran oxalate hydrate | 25 | 61 |
| propoxyphene (standard) | 3.9 | 50 |

The analgesic effect is achieved when the compounds of the invention are administered to a subject requiring such treatment at an effective oral, parenteral or intravenous dose of from 1 to 100 mg/kg of body weight per day. A preferred effective dose within this range is from about 15 to 50 mg/kg of body weight per day.

The compounds of the present invention are also useful as anticonvulsant agents for mammals as evidenced by the supra maximal electroshock assay of Woodbury, L. A. and Davenport, U. D. in Arch. Int. Pharmacodynam, Vol. 92 (1952) at pages 97–107.

In this method, groups of male mice are used (Charles River, CD-1), 18–30 grams. Drugs are prepared using distilled water and if insoluble, a surfactant is added. Control animals receive vehicle. Drugs are routinely administered intraperitoneally. The route of administration may be varied (orally, subcutaneously). The dosage volume is 10 ml/kg.

The animal's eyes are placed across the output terminals of an A.C. shocker that delivers 205 volts rms for 300 milliseconds. Electrode paste coats the animal's eyes at the point of contact with the terminals.

A compound is considered to give protection if the mouse does not exhibit extensor tonus. Protection is expressed as normalized percent inhibition relative to vehicle control.

A time response is carried out using 6 animals per group. Animals are tested at 30, 60 and 120 minutes post-drug. Additional time periods are tested if indicated by previous tests.

Listed below in Table II is the anticonvulsant effect of some of the compounds of the invention expressed as percent inhibition.

TABLE II

| Compound | Dose (subcutaneous) mg/kg | % Inhibition |
| --- | --- | --- |
| 4a-(3-dimethylaminopropyl)-1,2,3,4,4a,9b-hexahydrodibenzofuran hydrochloride | 28.1 | 50 ($ED_{50}$) |
| cis-1,2,3,4,4a,9b-hexahydro-4a-(3-methylaminopropyl)dibenzofuran hydrochloride | 27.7 | 50 ($ED_{50}$) |
| cis-1,2,3,4,4a,9b-hexahydro-4a-(2-dimethylaminoethyl)dibenzofuran hydrochloride | 22.4 | 50 ($ED_{50}$) |
| cis-1,2,3,4,4a,9b-hexahydro-4a-(2-methylaminoethyl)dibenzofuran hydrochloride | 41.7 | 50 ($ED_{50}$) |
| cis-1,2,3,4,4a,9b-hexahydro-4a-[3-(N—methyl-N—phenethylamino)-propyl]dibenzofuran hydrochloride | 25 | 50 |
| cis-1,2,3,4,4a,9b-hexahydro-4a-methylaminomethyldibenzofuran hydrochloride | 22.5 | 50 ($ED_{50}$) |
| Chlorodiazepoxide (standard) | 8.0 | 50 |
| Diazepam (standard) | 1.7 | 50 |

The anticonvulsant effect is achieved when the compounds of the invention are administered to a subject requiring such treatment at an effective oral, parenteral or intravenous dose of from 10 to 100 mg/kg of body weight per day. A preferred effective dose within this range is from about 20 to 50 mg/kg of body weight per day.

Selected compounds of the present invention are also useful in the treatment of depression in mammals, as demonstrated by their ability to inhibit tetrabenazine-induced depression in mice [International Journal of Neuropharmacology, 8 73 (1969)], a standard assay for useful antidepressent properties.

Listed below in Table III is the antidepressant effect of some of the compounds of the invention expressed as percent inhibition of the ptosis of tetrabenazine-induced depression in mice.

TABLE III

| Compound | Dose (Intraperitoneal mg/kg) | % Inhibition |
| --- | --- | --- |
| cis-1,2,3,4,4a,9b-hexahydro-4a-(3-methylaminopropyl)dibenzofuran hydrochloride | 5.9 | 50 ($ED_{50}$) |
| cis-1,2,3,4,4a,9b-hexahydro-4a-(2-dimethylaminoethyl)dibenzofuran hydrochloride | 20.0 | 70 |
| cis-1,2,3,4,4a,9b-hexahydro-4a-(2-methylaminoethyl)dibenzofuran hydrochloride | 20.0 | 60 |
| cis-1,2,3,4,4a,9b-hexahydro-4a-[2-[N—(3-methyl-2-butenyl)-N—methyl]aminoethyl]dibenzofuran oxalate | 20.0 | 77 |
| Amitriptyline (standard) | 2.0 | 50 |

The antidepressant effect is achieved when these compounds of the invention are administered to a subject requiring such treatment at an effective oral, parenteral or intravenous dose of from 1 to 100 mg/kg of body weight per day. A preferred effective dose within this range is from about 1 to 10 mg/kg of body weight per day.

It is to be understood, however, that for any particular subject, specific dosage regimens for the above-described analgesic, anticonvulsant and antidepressant activity should be adjusted according to the individual need and the professional judgement of the person administering or supervising the administration of the compounds of the invention. It is to be further understood that the dosages set forth herein are examples only and that they do not, to any extent limit the scope or practice of the invention.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for the purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of at least one compound of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the particular compound of the invention.

The tablets, pills, capsules, troches and the like may also contain the following adjuvants: a binder such as microcrystalline cellulose, gum tragacanth or gelatin; an excipient such as starch or lactose; a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the following adjuvants: a sterile diluent such as water for injection, saline solution, fixed oils, polyethylene glycols, glycerine, propylene glycol or other synthetic solvents: antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

EXAMPLE 1

(a) 1-(2-Fluorophenyl)cyclohexene

A solution of o-bromofluorobenzene (17.5 g; 0.10 mole) in 150 ml of dry tetrahydrofuran (THF) was chilled to −60° and n-butyllithium (50 ml of 2.4M; 0.12 mole) was added dropwise at a rate such that the reaction temperature did not rise above −55°. When the addition was complete a solution of cyclohexanone (10.0 g; 0.10 mole) in 50 ml of THF was added, again maintaining the reaction temperature below −55°. The reaction was then allowed to come to room temperature over 90 minutes and was quenched by the addition of 10 ml of saturated $NH_4Cl$ solution. An additional 400 ml of water was added, then the organic layer was separated and dried. The aqueous phase was extracted again with ethyl acetate, then the combined, dried, organic phases were concentrated to an oil. This oil was dissolved in 200 ml of glacial acetic acid and treated with 1 ml of concentrated $H_2SO_4$. The acetic acid was concentrated to about 30 ml on a rotary evaporator, then diluted with 250 ml of water and the solution made basic with 50% NaOH. Extraction with ether, followed by drying and concentration under reduced pressure gave an oil that was distilled at 0.15 mm to give 9.26 g (53%) of 1-(2-fluorophenyl)cyclohexene, b.p. 70°-72°, that was homogeneous to thin layer chromatography (TLC).

ANALYSIS: Calculated for $C_{12}H_{13}F$: 81.78%C, 7.43%H, 10.78%N. Found: 81.32%C, 7.71%H, 11.00%N.

(b) 1-(2-Fluorophenyl)cyclohexene oxide 1-(2-Fluorophenyl)cyclohexene of Example 1(a) [6.76 g; 0.038 mole] was dissolved in a two-phase system consisting of 350 ml of $CH_2Cl_2$ and 110 ml of 0.5M $NaHCO_3$. m-Chloroperbenzoic acid (7.80 g of 85%; 0.38 mole) was then added portionwise with vigorous mechanical stirring. After 2 hours TLC indicated that the reaction was complete. The organic layer was separated and washed with 100 ml of N NaOH and 100 ml of water. Drying and concentration under reduced pressure gave an oil which amounted to 6.34 g (86%) after distillation, b.p. 113°/0.075 mm (Kugelrohr). A small portion was chromatographed over silica gel ($CHCl_3$) to remove traces of polar impurities and distilled again to provide the sample of 1-(2-fluorophenyl)cyclohexene oxide.

ANALYSIS: Calculated for $C_{12}H_{13}FO$: 74.98%C, 6.82%H, 9.88%F. Found: 75.18%C, 6.84%H, 9.71%F.

(c) 2-(2-Fluorophenyl)cyclohexanone 1-(2-fluorophenyl)cyclohexanone oxide of Example 1(b) (25.0 g; 0.130 mole), was added over 5 minutes to 50 ml of concentrated $H_2SO_4$ that was stirring in an ice/water bath. After stirring in the cold for an additional 5 minutes the solution was allowed to come to room temperature over 15 minutes then poured over ice. This emulsion was made basic with 50% NaOH and then extracted several times with ether. The ether extracts were combined, dried ($MgSO_4$), and concentrated under reduced pressure to give an oil that crystallized upon scratching. Recrystallization from hexane gave 18.4 g (73%) of 2-(2-fluorophenyl)cyclohexanone, m.p. 47°-49°.

ANALYSIS: Calculated for $C_{12}H_{13}FO$: 74.98%C, 6.82%H, 9.88%F. Found: 74.99%C, 6.75%H, 9.99%F.

(d) cis-1-(3-Dimethylaminopropyl)-2-(2-fluorophenyl)cyclohexanolhydrochloride

A solution of 3-dimethylaminopropylmagnesium chloride was generated in 40 ml of dry tetrahydrofuran (THF) from 5.4 g (0.222 g-atom) of magnesium turnings and 25.5 g (0.210 mole) of freshly distilled 3-dimethylaminopropyl chloride.

2-(2-Fluorophenyl)cyclohexanone of Example 1(c) [17.60 g; 0.092 mole] was added in 100 ml of THF. The reaction mixture was then refluxed for 4 hours and allowed to stand overnight (about 16 hours). The solution was then poured into ice/5% HCl and extracted with methylene chloride. The aqueous phase was made basic with $NH_4OH$, extracted with methylene chloride, and the combined organic phases were dried ($MgSO_4$). Evaporation and distillation (143°-146°/0.1 mm) gave 15.26 g (60%) of the free base as an oil. The hydrochloride was formed by treating an ether solution of the free base with ethereal HCl and filtering. It was recrystallized from chloroform/ether to yield 1-(3-dimethylaminopropyl)-2-(2-fluorophenyl)cyclohexanol hydrochloride, m.p. 164°-166° C.

ANALYSIS: Calculated for $C_{17}H_{27}FNO \cdot HCl$: 64.64%C, 8.62%H, 4.43%N. Found: 64.51%C, 8.43%H, 4.29%N.

(e) cis-4a-(Dimethylaminopropyl)-1,2,3,4,4a,9b-hexahydrodibenzofuran hydrochloride 1-(3-Dimethylaminopropyl-2-(2-fluorophenyl)cyclohexanol of Example 1(d) (12.05 g; 43.1 mmole) was dissolved in 150 ml of dry benzene and NaH (2.1 g of 99%; 87.5 mmole) was added. This mixture was brought to reflux and monitored by thin layer chromatography (TLC) as portions of dimethylformamide (DMF) were added periodically. After 150 ml of DMF had been added (4.5 hours at reflux) no starting material remained, so the reaction was carefully quenched with water and extracted with three 300 ml portions of 10:1 hexane/ether. The combined extracts were washed three times with water, dried ($MgSO_4$), concentrated, and distilled (Kugelrohr, 145° C./0.1 mm) to give 9.47 g (85%) of an oil. Three grams of this oil was converted to the hydrochloride in ethereal HCl as in Example 1(d) and recrystallized from chloroform/ether to give 2.75 g of 4a-(3-dimethylaminopropyl)-1,2,3,4,4a,9b-hexahydrodibenzofuran hydrochloride, m.p. 135°–138° C.

ANALYSIS: Calculated for $C_{17}H_{25}NO.HCl$: 69.01%C, 8.86%H, 4.74%N. Found: 68.92%C, 9.06%H, 4.57%N.

EXAMPLE 2

(a)

cis-1,2,3,4,4a,9b-Hexahydro-4a-[3(N-methyl-N-phenoxycarbonyl)propylamino]dibenzofuran 4a-(3-Dimethylaminopropyl)-1,2,3,4,4a,9b-hexahydrodibenzofuran hydrochloride of Example 1(b) (5.20 g; 0.020 mole) was dissolved in 25 ml of $CaCl_2$ dried $CH_2Cl_2$ and phenyl chloroformate in 25 ml of $CH_2Cl_2$ was added dropwise. After stirring for 2 hours the reaction was refluxed briefly, the solvent removed, and the residue passed through a silica gel column ($CHCl_3$). The $CHCl_3$ was then removed under reduced pressure and the residue was heated for 15 minutes at 200° C. 0.05 mm to drive off volatile impurities, giving 5.39 g (74%) of 1,2,3,4,4a,9b-hexahydro-4a-[3-(N-methyl-N-phenoxycarbonyl)propylamino]dibenzofuran.

ANALYSIS: Calculated for $C_{23}H_{27}NO_3$: 75.58%C, 7.45%H, 3.83%N. Found: 75.75%C, 7.53%H, 3.69%N.

(b)

cis-1,2,3,4,4a,9b-Hexahydro-4a-(3-methylaminopropyl)-dibenzofuran 1,2,3,4,4a,9b-Hexahydro-N-methyl-N-phenoxycarbonyldibenzofuran-4a-propanamine of Example 2(a). (5.00 g; 13.7 mmole) was suspended in 50 ml of ethylene glycol and 5 ml of 30% NaOH was added. The reaction was then refluxed for 30 minutes and poured into water. The resulting emulsion was extracted with ether and then the ether extracts were washed with water and dried ($MgSO_4$). Concentration under reduced pressure gave 3.22 g of free base (94% yield). The hydrochloride was formed as in Example 1(d) by treatment with ethereal HCl and recrystallized from ether/chloroform to give 2.70 g of cis-1,2,3,4,4a,9b-hexahydro-4a-(3-methylaminopropyl)dibenzofuran (70% yield), m.p. 116°–120° C.

ANALYSIS: Calculated for $C_{16}H_{23}NO.HCl$: 68.19%C, 8.58%H, 4.97%N. Found: 67.83%C, 8.53%H, 4.80%N.

EXAMPLE 3 cis-1,2,3,4,4a,9b-Hexahydro-4a-[3-(N-propyl)-N-methyl)aminopropyl]dibenzofuran oxalate hydrate Bromopropane (2.51 gms, 0.0204 moles) was dissolved in 25.0 ml n-butylalcohol and slowly added to a stirring mixture of cis-1,2,3,4,4a,9b-hexahydro-4a-(3-methylaminopropyl)dibenzofuran of Example 2(b) (5.00 gms. 0.0204 mole) and $K_2CO_3$ (3.52 gms, 0.0355 mole) in 25.0 ml of n-butylalcohol. The mixture was refluxed for 1.0 hour, cooled, quenched with water and extracted into ether. The organic phase was washed with water, brine, dried over $MgSO_4$ and concentrated. An oil resulted (4.18 gms, 73.8% yield). The oxalate was formed by treating an ethereal solution of the free base with an equivalent amount of oxalic acid in ether and filtering. Upon recrystallization from ethyl acetate cis-1,2,3,4,4a,9b-hexahydro-4a-[3-(N-propyl)-N-methyl)aminopropyl]dibenzofuran oxalate hydrate was recovered, m.p. 88°–90° C.

ANALYSIS: Calculated for $C_{19}H_{29}NO.C_2H_2O_4.0.25H_2O$: 66.03%C, 8.25%H, 3.66%N. Found: 66.22%C, 8.14%H, 3.67%N.

EXAMPLE 4 cis-1,2,3,4,4a,9b-Hexahydro-4a-[3-(N-methyl-N-phenethylamino)propyl]dibenzofuran hydrochloride A solution of 2.6 g (0.011 mole) of cis-1,2,3,4,4a,9b-hexahydro-4a-(3-methylaminopropyl)dibenzofuran of Example 2(b) in 25 ml of $CHCl_3$ was stirred with 2.77 g (0.033 mole) of $NaHCO_3$ while 1.87 g (0.012 mole) of phenylacetyl chloride in 10 ml $CHCl_3$ was added dropwise. The temperature rose to 28° C. The reaction mixture was stirred 4 hours and allowed to stand overnight (about 16 hours). The $NaHCO_3$ was filtered off. The $CHCl_3$ was washed with 5% HCl followed by water, dried over $Na_2SO_4$ and evaporated to give 3.4 g of an amide. To 0.36 g (0.009 mole) of $LiAlH_4$ in 15 ml of dry THF was added dropwise a solution of 3.4 g (0.0094 mole) of the resultant amide in 15 ml of THF. The reaction mixture was refluxed 3 hours. The mixture was cooled, 0.5 ml of $H_2O$ added followed by 0.5 ml of 15% NaOH and 1.5 ml of water. The precipitate was filtered off and the filtrate extracted with ether and dried over $Na_2SO_4$. Evaporation of the ether gave 20 g of an amine. The amine was dissolved in ether and the hydrochloride was formed as in Example 1(b). Recrystallization from $CHCl_3$-ether yielded 1.52 g of cis-1,2,3,4,4a,9b-hexahydro-4a-[3-(N-methyl-N-phenethylamino)propyl]dibenzofuran, m.p. 148°–150° C.

ANALYSIS: Calculated for $C_{24}H_{31}NO.HCl$: 74.68%C, 8.36%H, 3.63%N. Found: 74.76%C, 8.44%H, 3.50%N.

EXAMPLE 5 cis-1,2,3,4,4a,9b-Hexahydro-4a-[3-(N-methyl-N-furfuryl)amino propyl]dibenzofuran oxalate hydrate To a stirring mixture of cis-1,2,3,4,4a,9b-hexahydro-4a-(3-methylaminopropyl)dibenzofuran of Example 2(b) (5.00 gm, 0.0204 mole) and $NaHCO_3$ (3.52 gms) in 25.0 ml of $CHCl_3$, was added cyclobutane carboxylic acid chloride (2.67 gms, 0.0204 mole) dissolved in 25.0 ml of $CHCl_3$. The mixture was allowed to stir at room temperature for 2 hours. The mixture was then filtered, the chloroform solution washed with dilute HCl, dilute $NaHCO_3$, dried over $MgSO_4$ and concentrated. The resulting oil (6.13 gms, 0.0181 mole) was reduced with lithium aluminum hydride (0.67 gms, 0.0181 mole) in 120 ml of dry tetrahydrofuran at reflux for two hours. The mixture was cooled, quenched with saturated $Na_2SO_4$, filtered. and concentrated. To the resultant oil (91.6%) in ether was added oxalic acid in ether to form the oxalate. Recrystallization from ethyl acetate yielded cis-1,2,3,4,4a,9b, hexahydro-4a-[3-(N-methyl-N-furfuryl)aminopropyl]dibenzofuran oxalate hydrate m.p. 78°–81° C.

ANALYSIS: Calculated for $C_{21}H_{25}NO_3C_2H_2O$: 65.77%C, 6.97%H, 3.34%N. Found: 65.73%C, 7.13%H, 3.33%N.

EXAMPLE 6 cis-1,2,3,4,4a,9b-Hexahydro-4a-[3-(N-(3-phenylpropyl)-N-methyl)aminopropyl]dibenzofuran oxalate hydrate 1-Bromo-3-phenylpropane (2.43 gms, 0.012 moles) was dissolved in 15.0 ml of n-butyl alcohol which was slowly added to a mixture of cis-1,2,3,4,4a,9b-hexahydro-4a-(3-methylaminopropyl)dibenzofuran of Example 2(b) (3.00 gms, 0.012 moles) and K$_2$CO$_3$ (2.40 gms, 0.024 moles) in 15.0 ml n-butylalcohol. The mixture was stirred for two hours and refluxed for 30 minutes. After cooling to room temperature the reaction mixture was quenched with water and extracted with chloroform. The organic phase was washed with water, brine, dried over MgSO$_4$ and concentrated to an oil (3.98 gms 89.7%). The oxalate was formed as in Example 4 and was recrystallized from ethyl acetate to yield cis-1,2,3,4,4a,9b-hexahydro-4a-[3-(N-(3-phenylpropyl)-N-methyl)aminopropyl]dibenzofuran oxalate hydrate, m.p. 101°–103° C.

ANALYSIS: Calculated for C$_{25}$H$_{33}$NO.C$_2$H$_2$O$_4$.0.75H$_2$O: 69.43%C, 7.87%H, 3.00%N. Found: 69.53%C, 7.62%H, 3.16%N.

EXAMPLE 7 cis-1,2,3,4,4a,9b-hexahydro-4a-[3-(N-cyclobutylmethyl-N-methyl)aminopropyl]dibenzofuran oxalate hydrate Cyclobutane carboxylic acid chloride (2.37 gms, 0.02 mole) dissolved in 20.0 ml CHCl$_3$ was slowly added to a stirring mixture of cis-1,2,3,4,4a,9b-hexahydro-4a-(3-methylaminopropyl)dibenzofuran of Example 2(b) (3.00 gms, 0.012 mole) and NaHCO$_3$ (6.00 gms, 0.071 mole) in 25.0 ml of CHCl$_3$ and refluxed for two hours. The mixture was filtered then the chloroform solution washed sequentially with dilute HCl, dilute NaHCO$_3$ and water. After drying over MgSO$_4$ and removal of the solvent the resultant amide was reduced with LiAlH$_4$ (0.31 gms, 0.008 moles) in 30.0 ml tetrahydrofuran (refluxed 4 hours). The mixture was cooled, quenched with Na$_2$SO$_4$ (saturated), filtered, dried over MgSO$_4$ and concentrated to give 1.99 gms (77.1%) of an oil. The oxalate was formed as in Example 4 and was recrystallized once from ethyl acetate to yield cis-1,2,3,4,4a,9b-hexahydro-4a-[3-(N-cyclobutylmethyl-N-methyl)aminopropyl]-dibenzofuran oxalate hydrate, m.p. 93°–96° C.

ANALYSIS: Calculated for C$_{21}$H$_{31}$NOC$_2$H$_2$O$_4$ 0.25H$_2$O: 67.70%C, 8.27%H, 3.43%N. Found: 67.78%C, 8.03%H, 3.39%N.

EXAMPLE 8

(a)

Cis-1-(3-Diethylaminopropyl)-2-(2-fluorophenyl)cyclohexanol hydrochloride Hemihydrate 3-Diethylaminopropyl grignard was generated from 2.67 g of Mg (0.11 g-atom) and 14.03 g of freshly distilled 3-diethylaminopropyl chloride (0.094 mole) in 60 ml of tetrahydrofuran (THF). The ketone (18.07 g; 0.094 mole) was added in 150 ml of THF and then the reaction was refluxed for 1 hour. It was then distributed between ether and 5% HCl and the aqueous was washed well with additional ether. The aqueous was then made basic with NH$_4$OH and extracted with ether. Scrupulous removal of the solvent gave 12.24 g of product as an oil (42.4%) that was primarily one component by thin layer chromatography in 1:1 acetone/methanol (Rf-0.32) with a trace impurity (Rf-0.15). Five grams of the oil were treated with ethereal HCl to give the crystalline hydrochloride. Recrystallization from CHCl$_3$/ether gave product, m.p. 124°–128°.

ANALYSIS: Calculated for C$_{19}$H$_{30}$FNO.HCl.0.5-H$_2$O: 64.66%C, 8.85%H, 3.97%N. Found 64.93%C, 9.01%H, 4.15%N.

(b)

cis-1,2,3,4,4a,9b-Hexahydro-4a-(3-diethylaminopropyl)-dibenzofuran oxalate cis-1-(3-Diethylaminopropyl)-2-(2-fluorophenyl)cyclohexanol of Example 8(a) (7.1 g; 0.02 mole) was refluxed for a total of 3 hours in 60 ml of 1:1 DMF/benzene containing 1.2 g of NaH (0.05 mole). The reaction was quenched with water and the product extracted into ether. It was filtered two times over 20 g of silica gel (H$_2$O) to yield 4.77 g ((72.3%) of product which was treated in the same manner as in Example 4 to form the oxalate. The oxalate was recrystallized from ethyl acetate/isopropyl alcohol to yield cis-1,2,3,4,4a,9b-hexahydro-4a-(3-diethylaminopropyl)dibenzofuran oxalate, m.p. 111°–115° C.

ANALYSIS: Calculated for C$_{19}$H$_{29}$NOC$_2$H$_2$O$_4$: 66.82%C, 8.28%H, 3.71%N. Found: 66.53%C, 8.26%H, 3.61%N.

EXAMPLE 9

(a)

cis-2-(2-Fluorophenyl)-1-(3-piperidinopropyl)cyclohexanol hydrochloride

A grignard reagent was generated from 2.2 g of Mg (0.091 g-atom) and 11.0 g of freshly distilled N-(3-chloropropyl)piperidine in a total of 70 ml of tetrahydrofuran. 2-(2-Fluorophenyl)cyclohexanone of Example 1(d) (7.0 g; 0.036 mole) was added in 60 ml of THF and the reaction was refluxed for 3 hours. It was poured into 5% HCl and washed with ether, then made basic with aqueous NH$_3$ and extracted with ether. Drying and scrupulous removal of the solvents gave 7.05 g (61%) of the free base as an oil. The hydrochloride formed smoothly as in Example 1(d) and was recrystallized from CHCl$_3$/ether to give cis-2-(2-fluorophenyl)-1-(3-piperidinopropyl)cyclohexanol hydrochloride.

ANALYSIS: Calculated for C$_{20}$H$_{30}$FNO.HCl: 67.49%C, 8.78%H, 3.94%N. Found: 67.15%C, 8.85%H, 3.73%N.

(b)

cis-1,2,3,4,4a,9b-hexahydro-4a-(3-piperidinopropyl)-dibenzofuran oxalate cis-2-(2-Fluorophenyl)-1-(3-piperidinopropyl)cyclohexanol of Example 9(a) (3.20 g; 0.01 mole) was dissolved in 10 ml of DMF and added to a suspension of NaH (0.6 g of 50% dispersion; 0.013 mole) in 20 ml of DMF. The reaction was warmed one hour at 70° C. and then poured into water and extracted into ether. Evaporation gave an oil that was chromatographed over 100 g of silica gel (1:1 acetone/methanol) to yield 2.45 g (82%) of an oil. The oxalate was formed as in Example 4 in ether and was recrystallized from ethyl acetate to give cis-1,2,3,4,4a,9b-hexahydro-4a-(3-piperidinopropyl)dibenzofuran oxalate, m.p. 160°–164° C.

ANALYSIS: Calculated for C$_{20}$H$_{29}$NO.C$_2$H$_2$O$_4$: 67.84%C, 8.02%H, 3.60%N. Found: 67.56%C, 8.01%H, 3.47%N.

EXAMPLE 10

(a)

trans-N,N-Dimethyl-[1-hydroxy-2-(2-fluorophenyl)cyclohexyl]acetamide

A solution of lithium diisopropylamide was prepared by adding n-butyllithium (53.8 ml of 2.6M; 0.140 mole) to a solution of diisopropylamine (12.15 g; 0.140 mole)

in 150 ml of tetrahydrofuran (THF), chilled to 3°–5° C. After stirring at this temperature for 1 hour, N,N-dimethyl acetamide (10.30 g; 0.118 mole) in 40 ml of THF tetrahydrofuran was added and the solution was allowed to come to room temperature over 1.5 hours. At the end of this time 2-(2-fluorophenyl)cyclohexanone of Example 1(d) (18.20 g; 0.095 mole) in 50 ml of THF tetrahydrofuran was added and the reaction was stirred an additional 1.5 hours, then poured into ice/5% HCl. The THF was separated and the organic phase was extracted again with ethyl acetate. The combined, dried (MgSO$_4$) organic phase was concentrated to an oil that crystallized upon scratching. Trituration with hexane gave 17.70 g (67%) of trans-N,N-dimethyl-[1-hydroxy-2-(2-fluorophenyl)cyclohexyl]acetamide, m.p. 68°–71° C. After one crystallization from hexane the m.p. was 71°–73° C.

ANALYSIS: Calculated for $C_{16}H_{22}FNO_2$: 68.79%C, 7.94%H, 5.02%N. Found: 69.01%C, 7.95%H, 4.79%N.

(b)
trans-1-(2-Dimethylaminoethyl)-2-(2-fluorophenyl)cyclohexanol hydrochloride

A solution of trans-N,N-dimethyl-[1-hydroxy-2-(2-fluorophenyl)cyclohexyl]acetamide of Example 10(a) (8.25 g; 0.030 mole) in 25 ml of dry THF was added to a suspension of lithium aluminum hydride (1.20 g; 0.032 mole) in 25 ml of THF and brought to reflux. After 1.5 hours at reflux, thin layer chromatography (TLC) showed no starting amide so the reaction was quenched with 1.2 ml H$_2$O, 1.2 ml 15% NaOH, then 3.6 ml H$_2$O. The solution was filtered and the salts were washed well with hot THF. Evaporation of the combined THF filtrates, followed by Kugelrohr distillation (145° C., 0.075 mm) gave 7.57 g (97%) of free base that was homogeneous to TLC. 500 mg of free base were converted to the hydrochloride with ethereal HCl as in Example 1(d). Recrystallization from CHCl$_3$/ether gave trans-1-(2-dimethylaminoethyl)-2-(2-fluorophenyl)cyclohexanol hydrochloride, m.p. 157°–159° C.

ANALYSIS: Calculated for $C_{16}H_{24}FNO.HCl$: 63.66%C, 8.35%H, 4.64%N. Found: 63.61%C, 8.07%H, 4.87%N.

(c)
cis-4a-(2-Dimethylaminoethyl)-1,2,3,4,4a,9b-Hexahydrodibenzofuran hydrochloride Trans-1-(2-dimethylaminoethyl)-2-(2-fluorophenyl)cyclohexanol of Example 10(b) (6.86 g; 25.9 mmole) was dissolved in 75 ml of CaCl$_2$ dried benzene and sodium hydride (1.0 g from freshly washed 50% oil dispersion; 41.7 mmole) was added. The reaction was heated to reflux and 75 ml of sieve-dried DMF was added. After 45 minutes TLC indicated complete reaction. The reaction was poured into water and extracted with ether. The combined ether extracts were washed several times with water, once with brine and then dried (MgSO$_4$). Evaporation and Kugelrohr distillation (142° C./0.05 mm) gave 5.62 g (88%) of free base. Two and one half grams were converted to the hydrochloride with etheral HCl as in Example 1(b). Two recrystallizations from CHCl$_3$/ether gave 2.2 g of cis-1,2,3,4,4a,9b-hexahydro-4a-(2-dimethylaminoethyl)dibenzofuran hydrochloride, m.p. 268°–270° C.

ANALYSIS: Calculated for $C_{16}H_{23}NO.HCl$: 68.19%C, 8.58%H, 4.97%N. Found: 67.72%C, 8.65%H, 4.76%N.

EXAMPLE 11 cis-1,2,3,4,4a,9b-Hexahydro-4a-(2-methylaminoethyl)-dibenzofuran hydrochloride cis-4a-(2-Dimethylaminoethyl)-1,2,3,4,4a,9b-hexahydrodibenzofuran of Example 10(c) (15.42 g; 0.063 mole) was dissolved in 30 ml of CaCl$_2$ dried CH$_2$Cl$_2$ and phenyl chloroformate (10.8 g; 0.069 mole) in 30 ml of CH$_2$Cl$_2$ was added dropwise. After two hours an additional 0.5 g phenyl chloroformate was added and the reaction was refluxed for one hour. Ethyl acetate (250 ml) was added and the solution was washed twice with 4N NaOH, twice with 2N HCl, and once with water. Removal of the solvents (0.1 mm; 50° C.) gave 17.56 g of a carbamate (79%). This carbamate was suspended in a solution made from 16 g KOH, 8 ml H$_2$O, and 160 ml of ethylene glycol. This mixture was refluxed for 30 minutes and then poured into water and extracted with ether. The combined ether extracts were washed several times with water and once with brine. Drying (MgSO$_4$) and removal of the solvent (again at 0.1 mm) gave 9.75 g (76%) of a free base (60% from the dimethylamine). The free base was converted to the hydrochloride as in Example 1(b). One recrystallization from CHCl$_3$/ether gave cis-1,2,3,4,4a,9b-hexahydro-4a-(2-methylaminoethyl)dibenzofuran hydrochloride, m.p. 173°–175° C.

ANALYSIS: Calculated for $C_{15}H_{21}NO.HCl$: 67.27%C, 8.28%H, 5.23%N. Found: 67.05%C, 8.21%H, 5.05%N.

EXAMPLE 12 cis-1,2,3,4,4a,9b-Hexahydro-4a-[2-(N-(3-methyl-2-butenyl)-N-methyl)aminoethyl]dibenzofuran oxalate Cis-1,2,3,4,4a,9b-hexahydro-4a-(2-methylaminoethyl)dibenzofuran of Example 11 (3.0 g; 0.013 mole) was dissolved in 30 ml of DMF containing 2.0 g of K$_2$CO$_3$ (0.0145 mole). This solution was warmed to 80° C. and a solution of 1-bromo-3-methyl-2-butene (1.93 g; 0.013 mole) in 15 ml DMF was added dropwise. After 15 minutes the reacttion was poured into water and extracted into ether. The resultant product obtained from the dried ether extract was chromatographed over 250 g of alumina (1:1 ether/hexane) to obtain 1.50 g of product as the free base. Reaction with oxalic acid in ether as in Example 4 gave 1.65 g of cis-1,2,3,4,4a,9b-hexahydro-4a-[2-(N-(3-methyl-2-butenyl)-N-methyl)aminoethyl]dibenzofuran oxalate, m.p. 126°–130° C. Recrystallization from ethyl acetate yielded product having a melting point of 127°–129° C.

ANALYSIS: Calculated for $C_{20}H_{29}NO.C_2H_2O_4$: 67.84%C, 8.02%H, 3.60%N. Found: 67.45%C, 8.00%H, 3.56%N.

EXAMPLE 13

Cis-1,2,3,4,4a,9b-hexahydro-4a-[2-{N-methyl-N-(3-phenoxypropyl)}aminoethyl]dibenzofuran oxalate Cis-1,2,3,4,4a,9b-hexahydro-4a-(2-methylaminoethyl)dibenzofuran (2.0 g; 8.65 mmole) of Example 11 was dissolved in 10 ml of DMF and 3-phenoxypropylbromide (2.23 g; 10.0 mmole) was added, along with K$_2$CO$_3$ (1.52 g; 11.0 mmole). The reaction was warmed at 66° C. for 2.5 hours and then poured into water and extracted into ether. After drying and evaporating the solvent, the resulting oil was treated with oxalic acid in ether as in Example 4 to give the oxalate. After one recrystallization from ethylacetate, 1.28 g (32%) of cis-1,2,3,4,4a,9b-hexahydro-4a-[2-[N-methyl-N-(3-phenoxypropyl)]aminoethyl]dibenzofuran oxalate was obtained as the hemihydrate, m.p. 96°–98° C.

ANALYSIS: Calculated for $C_{24}H_{31}NO_2 \cdot (CO_2H)_2 0.5H_2O$: 67.22%C, 7.38%H, 3.02%N. Found: 67.46%C, 7.26%H, 3.03%N.

EXAMPLE 14 cis-1,2,3,4,4a,9b-Hexahydro-4a-[2-[N-(3-phenylpropyl)-N-methylamino]ethyl]dibenzofuran oxalate hemihydrate To a mixture of 4.08 g (0.018 m) of cis-1,2,3,4,4a,9b-hexahydro-4a-(2-methylaminoethyl)dibenzofuran of Example 11 and 4.38 g (0.022 m) of 1-bromo-3-phenylpropane in 60 ml DMF, 3.8 g (0.045 m) of $NaHCO_3$ was added under nitrogen. The reaction mixture was warmed to 87° C. and held there overnight (about 16 hours). The temperature was raised to 108° C. for 4 hours, the $NaHCO_3$ filtered off and the mixture partitioned between water and ethyl acetate. The ethylacetate layer was dried over $Na_2SO_4$ and evaporated to give an oil. The resultant oil was converted to an oxalate in ether as in Example 4 and recrystallized from ethyl acetate to give 2.2 g (28%) of cis-1,2,3,4,4a,9b-hexahydro-4a-[2-[-N-(3-phenylpropyl)-N-methylamino]ethyl]dibenzofuran oxalate hemihydrate m.p. 104°–105° C.

ANALYSIS: Calculated for $C_{24}H_{29}NO \cdot C_2H_2O_4 \cdot \frac{1}{2} H_2O$: 69.93%C, 7.22%H, 3.14%N. Found: 70.36%C, 7.28%H, 2.83%N.

EXAMPLE 15 cis-1,2,3,4,4a,9b-Hexahydro-4a-[2-(N-methyl-N-phenethyl)aminoethyl]dibenzofuran hydrochloride cis-1,2,3,4,4a,9b-hexahydro-4a-(2-methylaminoethyl)dibenzofuran of Example 11 (3.89 g; 0.017 mole) was dissolved in 40 ml of $CHCl_3$ and treated with 2.94 g of phenylacetyl chloride (0.019 mole) and 4.2 g (0.05 mole) of $NaHCO_3$. This suspension was stirred 1 hour then filtered and washed with 10% $K_2CO_3$ and 5% HCl. Drying and evaporation gave 6 g of an amide. The amide was reduced with 0.64 g (0.0169 mole) of $LiAlH_4$ in 25 ml of tetrahydrofuran (refluxed 1 hour). After quenching and concentration under reduced pressure 4.71 g of a free base was obtained. This free base was converted to an oxalate as in Example 4 which was recrystallized from ethanol, m.p. 164°–166° C.

The pure oxalate was neutralized with NaOH to yield a colorless oil that gave a hydrochloride upon treatment with ethereal HCl as in Example 1(b). After recrystallization from toluene, 1.32 g cis-1,2,3,4,4a,9b-hexahydro-4a-[2-(N-methyl-N-phenethyl)aminoethyl]dibenzofuran hydrochloride were obtained (21%), m.p. 129°–132° C.

ANALYSIS: Calculated for $C_{23}H_{29}NO \cdot HCl$: 74.27%C, 8.13%H, 3.77%N. Found: 74.05%C, 8.10%H, 3.81%N.

EXAMPLE 16

(a) cis-4-(2-Fluorophenyl)-1-oxaspiro[2.5]octane

Sodium hydride (1.32 g; 0.055 mole) was added to 60 ml of sieve-dried dimethylsulfoxide (DMSO) under a nitrogen atmosphere. To this was added trimethylsulfoxonium iodide (12.65 g; 0.057 mole) over a 10 minute period. The reaction mixture was then stirred for 2.5 hours at which time hydrogen evolution had ceased. 2-(2-Fluorophenyl)cyclohexanone of Example 1(d) (9.60 g; 0.050 mole) in 20 ml of DMSO was added over 5 minutes then the reaction was stirred 15 minutes at room temperature and 30 minutes at 60° C. It was poured into water and extracted with ether. The combined ether extracts were washed with water, then with brine, and dried ($MgSO_4$). Concentration and Kugelrohr distillation (130° C. 70.05 mm) gave 9.91 g (96%) of cis-4-(2-fluorophenyl)-1-oxaspiro[2.5]octane product as an oil.

ANALYSIS: Calculated for $C_{13}H_{15}FO$: 75.70%C, 7.33%H. Found: 75.54%C, 6.97%H.

(b) Cis-1-dimethylaminomethyl-2-(2-fluorophenyl)cyclohexanol

A small Parr bomb with a 3000 pound rupture disk was chilled to $-10°$ (ice/methanol) and charged with 6.66 g (0.032 mole) of cis-4-(2-fluorophenyl)-1-oxaspiro[2.5]octane of Example 16(a) and about 30 ml of dimethylamine (ca. 20 g; 0.45 mole). It was sealed and heated at 60° C. for 4 hours and then 90° C. for four additional hours. Kugelrohr distillation of the residue gave 7.97 g (98%) of product. A small amount of the residue was converted to the hydrochloride with ethereal HCl as in Example 1(d). Recrystallization from $CHCl_3$/ether gave cis-1-dimethylaminomethyl-2-(2-fluorophenyl)cyclohexanol, m.p. 223°–225° C.

ANALYSIS: Calculated for $C_{15}H_{22}FNO \cdot HCl$: 62.59%C, 8.06%H, 4.87%N. Found: 62.79%C, 8.15%H, 4.68%N.

(c) Cis-1,2,3,4,4a,9b-hexahydro-4a-dimethylaminomethyldibenzofuran hydrochloride Cis-1-dimethylaminomethyl-2-(2-fluorophenyl)cyclohexanol of Example 16(b) (6.72 g; 26.7 mmole) was dissolved in 50 ml of $CaCl_2$-dried benzene and sodium hydride (1.0 g; 41.7 mmole) was added. The reaction was heated to reflux and 50 ml of sieve-dried DMF was added. After 45 minutes at reflux TLC showed complete reaction. The reaction mixture was poured into water and extracted with ether. The ether extracts were washed well with water and then dried ($MgSO_4$). Evaporation of the solvent (0.1 mm; 50° C.) gave 6.04 g (98%) of free base.

Some free base (2.3 g) was converted to the hydrochloride in ethereal/HCl as in Example 1(b). One recrystallization from $CHCl_3$/ether gave cis-1,2,3,4,4a,9b-hexahydro-4a-dimethylaminomethyldibenzofuran hydrochloride, m.p. 200°–204° C.

ANALYSIS: Calculated for $C_{15}H_{21}NO \cdot HCl$: 67.27%C, 8.28%H, 5.23%N. Found: 67.11%C, 8.33%H, 5.34%N.

EXAMPLE 17 cis-1,2,3,4,4a,9b-Hexahydro-4a-methylaminomethyldibenzofuran hydrochloride

Cis-1,2,3,4,4a,9b-hexahydro-4a-dimethylaminomethyldibenzofuran of Example 16(c) (3.55 g; 0.015 mole) was dissolved in 7 ml of $CH_2Cl_2$ and phenyl chloroformate (3.2 g; 0.020 mole) in 7 ml of $CH_2Cl_2$ was added. The reaction was stirred for two hours at room temperature and then refluxed for one hour. Ethyl acetate was added and this solution was washed twice with 4N NaOH, twice with 2N and once with water. Drying ($MgSO_4$) and concentration under reduced pressure gave an oil. The oil was hydrolyzed by refluxing for a total of one hour in a solution of 6 g of KOH, 3 ml of H₂O, and 50 ml of ethylene glycol. It was poured into water, extracted with ether, and washed well with water. The crude amine obtained upon drying and evaporation gave a hydrochloride upon treatment with ethereal HCl as in Example 1(b). The hydrochloride was insoluble in hot $CHCl_3$ so methanol was added to obtain dissolution, then ether was added to cloudiness. Obtained in this manner was 2.13 g of cis-1,2,3,4,4a,9b-hexahydro-4a-methylaminomethyldibenzofuran hydrochloride (55%), m.p. 237°–239° C.

ANALYSIS: Calculated for $C_{14}H_{19}NO \cdot HCl$: 66.26%C, 7.94%H, 5.52%N. Found: 66.26%C, 7.78%H, 5.53%N.

I claim:

1. A compound of the formula

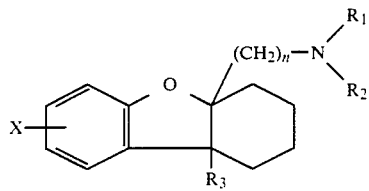

where X is hydrogen, loweralkyl, F, and Cl; $R_1$ is hydrogen, loweralkyl, arylloweralkyl having a formula of

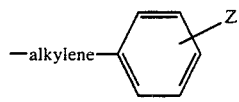

where Z is hydrogen, halogen, loweralkyl, loweralkoxy, $CF_3$ and $NH_2$; loweralkenyl, loweralkoxyloweralkyl, aryloxyloweralkyl having a formula of

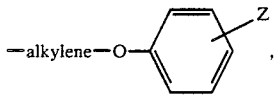

where Z is hydrogen, halogen, loweralkyl, loweralkoxy, $CF_3$ and $NH_2$; cycloalkylloweralkyl and heteroarylloweralkyl, wherein said heteroaryl group of said heteroarylloweralkyl group is selected from the group consisting of furyl, thienyl, pyrrolyl, pyrazolyl, imidazolyl, triazolyl, pyridinyl, pyridazinyl, pyrimidinyl, pyrazinyl, oxazinyl, oxazolyl, isoxazolyl, thiazolyl and isothiazolyl; $R_2$ is hydrogen, loweralkyl or $R_1$ and $R_2$ taken together with the N atom to which they are attached constitute a saturated heterocyclic ring having 5 or 6 members selected from the group consisting of piperidyl, pyrrolidyl, morpholino, thiomorpholino, and piperazinyl; $R_3$ is hydrogen, loweralkyl; and n is an integer of 1 to 3; the pharmaceutically acceptable acid addition salts thereof and where applicable, the stereo, optical and geometrical isomers of the foregoing.

2. The compound as defined in claim 1 which is 4a-(3-dimethylaminopropyl)-1,2,3,4,4a,9b-hexahydrodibenzofuran or a pharmaceutically acceptable acid addition salt thereof.

3. The compound as defined in claim 1 which is 1,2,3,4,4a,9b-hexahydro-4a-(3-methylaminopropyl)-dibenzofuran or a pharmaceutically acceptable acid addition salt thereof.

4. The compound as defined in claim 1 which is 1,2,3,4,4a,9b-hexahydro-4a-[3-N-propyl-N-methyl-)aminopropyl]dibenzofuran or a pharmaceutically acceptable acid addition salt thereof.

5. The compound as defined in claim 1 which is 1,2,3,4,4a,9b-hexahydro-4a-[3-(N-methyl-N-phenethylamino)propyl]dibenzofuran or a pharmaceutically acceptable acid addition salt thereof.

6. The compound as defined in claim 1 which is 1,2,3,4,4a,9b-hexahydro-4a-[3-(N-methyl-N-furfuryl-)aminopropyl]dibenzofuran or a pharmaceutically acceptable acid addition salt thereof.

7. The compound as defined in claim 1 which is 1,2,3,4,4a,9b-hexahydro-4a-[3-(N-(3-phenylpropyl)-N-methyl)aminopropyl]dibenzofuran or a pharmaceutically acceptable acid addition salt thereof.

8. The compound as defined in claim 1 which is 1,2,3,4,4a,9b-hexahydro-4a-[3-(N-cyclobutylmethyl-N-methyl)aminopropyl]dibenzofuran or a pharmaceutically acceptable acid addition salt thereof.

9. The compound as defined in claim 1 which is 1,2,3,4,4a,9b-hexahydro-4a-(3-diethylaminopropyl)-dibenzofuran or a pharmaceutically acceptable acid addition salt thereof.

10. The compound as defined in claim 1 which is 1,2,3,4,4a,9b-hexahydro-4a-(3-piperidinopropyl)dibenzofuran or a pharmaceutically acceptable acid addition salt thereof.

11. The compound as defined in claim 1 which is 1,2,3,4,4a,9b-hexahydro-4a-(2-dimethylaminoethyl)-dibenzofuran or a pharmaceutically acceptable acid addition salt thereof.

12. The compound as defined in claim 1 which is 1,2,3,4,4a,9b-hexahydro-4a-(2-methylaminoethyl)dibenzofuran or a pharmaceutically acceptable acid addition salt thereof.

13. The compound as defined in claim 1 which is 1,2,3,4,4a,9b-hexahydro-4a-[2-(N-methyl-2-butenyl)-N-methyl)aminoethyl]dibenzofuran or a pharmaceutically acceptable acid addition salt thereof.

14. The compound as defined in claim 1 which is 1,2,3,4,4a,9b-hexahydro-4a-[2-[N-methyl-N-(3-phenoxypropyl)]aminoethyl]dibenzofuran or a pharmaceutically acceptable acid addition salt thereof.

15. The compound as defined in claim 1 which is 1,2,3,4,4a,9b-hexahydro-4a-[2-[(3-phenylpropyl)methylamino]methyl]dibenzofuran or a pharmaceutically acceptable acid addition salt thereof.

16. The compound as defined in claim 1 which is 1,2,3,4,4a,9b-hexahydro-4a-(2-methylphenethylaminoethyl)dibenzofuran or a pharmaceutically acceptable acid addition salt thereof.

17. The compound as defined in claim 1 which is 1,2,3,4,4a,9b-hexahydro-4a-methylaminomethyldibenzofuran or a pharmaceutically acceptable acid addition salt thereof.

18. The compound as defined in claim 1 which is 1,2,3,4,4a,9b-hexahydro-4a-dimethylaminodibenzofuran or a pharmaceutically acceptable acid addition salt thereof.

19. An analgesic or anticonvulsant or antidepressant composition which comprises an effective pain alleviating amount or effective convulsion alleviating amount or effective antidepressant amount of a compound defined in claim 1 and a pharmaceutically acceptable carrier therefor.

20. The composition as defined in claim 19 which comprises 4a-(3-dimethyl-aminopropyl)-1,2,3,4,4a,9b-hexahydrodibenzofuran or a pharmaceutically acceptable acid addition salt thereof.

21. The composition as defined in claim 19 which comprises 1,2,3,4,4a,9b-hexahydro-4a-(3-methylaminopropyl)dibenzofuran or a pharmaceutically acceptable acid addition salt thereof.

22. The composition as defined in claim 19 which comprises 1,2,3,4,4a,9b-hexahydro-4a-[3-N-propyl-N-methyl)aminopropyl]dibenzofuran or a pharmaceutically acceptable acid addition salt thereof.

23. The composition as defined in claim 19 which comprises 1,2,3,4,4a,9b-hexahydro-4a-[3-(N-methyl-N-phenethylamino)propyl]dibenzofuran or a pharmaceutically acceptable acid addition salt thereof.

24. The composition as defined in claim 19 which comprises 1,2,3,4,4a,9b-hexahydro-4a-[3-(N-methyl-N-furfuryl)aminopropyl]dibenzofuran or a pharmaceutically acceptable acid addition salt thereof.

25. The composition as defined in claim 19 which comprises 1,2,3,4,4a,9b-hexahydro-4a-[3-(N-(3-phenylpropyl)-N-methyl)aminopropyl]-dibenzofuran or a pharmaceutically acceptable acid addition salt thereof.

26. The composition as defined in claim 19 which comprises 1,2,3,4,4a,9b-hexahydro-4a-[3-(N-cyclobutylmethyl-N-methyl)aminopropyl]-dibenzofuran or a pharmaceutically acceptable acid addition salt thereof.

27. The composition as defined in claim 19 which comprises 1,2,3,4,4a,9b-hexahydro-4a-(3-diethylaminopropyl)dibenzofuran or a pharmaceutically acceptable acid addition salt thereof.

28. The composition as defined in claim 19 which comprises 1,2,3,4,4a,9b-hexahydro-4a-(3-piperidinopropyl)dibenzofuran or a pharmaceutically acceptable acid addition salt thereof.

29. The composition as defined in claim 19 which comprises 1,2,3,4,4a,9b-hexahydro-4a-(2-dimethylaminoethyl)dibenzofuran or a pharmaceutically acceptable acid addition salt thereof.

30. The composition as defined in claim 19 which comprises 1,2,3,4,4a,9b-hexahydro-4a-(2-methylaminoethyl)dibenzofuran or a pharmaceutically acceptable acid addition salt thereof.

31. The composition as defined in claim 19 which comprises 1,2,3,4,4a,9b-hexahydro-4a-[2-(N-methyl-2-butenyl)-N-methyl)aminoethyl]-dibenzofuran or a pharmaceutically acceptable acid addition salt thereof.

32. The composition as defined in claim 19 which comprises 1,2,3,4,4a,9b-hexahydro-4a-[2-[N-methyl-N-(3-phenoxypropyl)]aminoethyl]-dibenzofuran or a pharmaceutically acceptable acid addition salt thereof.

33. The composition as defined in claim 19 which comprises 1,2,3,4,4a,9b-hexahydro-4a-[2-[(3-phenylpropyl)methylamino]ethyl]-dibenzofuran or a pharmaceutically acceptable acid addition salt thereof.

34. The composition as defined in claim 19 which comprises 1,2,3,4,4a,9b-hexahydro-4a-(2-methylphenethylaminoethyl)dibenzofuran or a pharmaceutically acceptable acid addition salt thereof.

35. The composition as defined in claim 19 which comprises 1,2,3,4,4a,9b-hexahydro-4a-methylaminomethyldibenzofuran or a pharmaceutically acceptable acid addition salt thereof.

36. The composition as defined in claim 19 which comprises 1,2,3,4,4a,9b-hexahydro-4a-dimethylaminodibenzofuran or a pharmaceutically acceptable acid addition salt thereof.

37. A method of treatment which comprises administering to a patient in need of relief from (a) pain, (b) convulsion or (c) depression a pharmaceutically effective amount for alleviating (a), (b), or (c) of a compound defined in claim 1.

38. The compound as defined in claim 1 wherein
(a) said arylloweralkyl is selected from the group consisting of phenylloweralkyl, o-tolylloweralkyl and m-methoxyphenylloweralkyl; and
(b) said aryloxyloweralkyl is selected from the group consisting of phenyloxyloweralkyl, o-tolyloxyloweralkyl and m-methoxyloweralkyl.

* * * * *